United States Patent
Yatvin et al.

(10) Patent No.: US 7,045,543 B2
(45) Date of Patent: May 16, 2006

(54) COVALENT CONJUGATES OF BIOLOGICALLY-ACTIVE COMPOUNDS WITH AMINO ACIDS AND AMINO ACID DERIVATIVES FOR TARGETING TO PHYSIOLOGICALLY-PROTECTED SITES

(75) Inventors: Milton B. Yatvin, Portland, OR (US); Richard L. Pederson, San Gabriel, CA (US)

(73) Assignee: EnzRel Inc., Portland, OR (US)

( * ) Notice: Subject to any disclaimer, the term of this patent is extended or adjusted under 35 U.S.C. 154(b) by 0 days.

(21) Appl. No.: 09/993,976

(22) Filed: Nov. 5, 2001

(65) Prior Publication Data

US 2003/0087803 A1    May 8, 2003

(51) Int. Cl.
*A01N 43/38* (2006.01)
*A01N 37/18* (2006.01)
*A61K 31/405* (2006.01)
*A61K 31/40* (2006.01)
*A61K 38/00* (2006.01)

(52) U.S. Cl. .......................... 514/415; 514/419; 514/2
(58) Field of Classification Search ................ 514/2, 514/78, 557, 885, 649, 415, 419; 424/450
See application file for complete search history.

(56) References Cited

U.S. PATENT DOCUMENTS

| | | | |
|---|---|---|---|
| 5,017,566 A | 5/1991 | Bodor | |
| 5,023,252 A | 6/1991 | Hseih | |
| 5,024,998 A | 6/1991 | Bodor | |
| 5,039,794 A | 8/1991 | Wier et al. | |
| 5,112,863 A | 5/1992 | Hashimoto et al. | |
| 5,124,146 A | 6/1992 | Neuwelt | |
| 5,149,794 A * | 9/1992 | Yatvin et al. | 536/29 |
| 5,153,179 A | 10/1992 | Eibl | |
| 5,177,064 A | 1/1993 | Bodor | |
| 5,223,263 A | 6/1993 | Hostetler et al. | |
| 5,254,342 A | 10/1993 | Shen et al. | |
| 5,256,641 A | 10/1993 | Yatvin et al. | |
| 5,258,404 A | 11/1993 | Ichinose et al. | |
| 5,270,312 A | 12/1993 | Glase et al. | |
| 5,284,876 A | 2/1994 | Shashoun et al. | |
| 5,389,623 A | 2/1995 | Bodor | |
| 5,405,834 A | 4/1995 | Bundgaard et al. | |
| 5,413,996 A | 5/1995 | Bodor | |
| 5,434,137 A | 7/1995 | Black | |
| 5,442,043 A | 8/1995 | Fukuta et al. | |
| 5,466,683 A | 11/1995 | Sterling et al. | |
| 5,484,809 A | 1/1996 | Hostetler et al. | |
| 5,484,911 A | 1/1996 | Hong et al. | |
| 5,512,671 A | 4/1996 | Piantadosi et al. | |
| 5,525,727 A | 6/1996 | Bodor | |
| 5,543,389 A * | 8/1996 | Yatvin et al. | 514/2 |
| 5,554,728 A | 9/1996 | Basava et al. | |
| 5,563,257 A | 10/1996 | Zilch et al. | |
| 5,580,571 A | 12/1996 | Hostetler | |
| 5,696,097 A | 12/1997 | Matsuda et al. | |
| 5,744,461 A | 4/1998 | Hostetler et al. | |
| 5,744,592 A | 4/1998 | Hostetler et al. | |
| 5,756,116 A | 5/1998 | Hostetler et al. | |
| 5,756,711 A | 5/1998 | Zilch et al. | |
| 5,827,819 A * | 10/1998 | Yatvin et al. | 514/2 |
| 5,827,831 A | 10/1998 | Hostetler et al. | |

FOREIGN PATENT DOCUMENTS

| | | |
|---|---|---|
| WO | WO 85/02342 A1 | 6/1985 |
| WO | WO 89/11299 A1 | 4/1991 |
| WO | WO 91/14438 A1 | 10/1991 |
| WO | WO 94/01131 A1 | 1/1994 |
| WO | WO 94/02178 A1 | 2/1994 |
| WO | WO 94/03424 A1 | 2/1994 |
| WO | WO 94/06450 A1 | 3/1994 |
| WO | WO 95/07092 A1 | 3/1995 |
| WO | WO 96/00537 A1 | 1/1996 |
| WO | WO 96/04001 A1 | 2/1996 |
| WO | WO 96/22303 A1 | 7/1996 |
| WO | WO 98/03204 A1 | 1/1998 |
| WO | WO 98/17325 A3 | 4/1998 |

OTHER PUBLICATIONS

Hardman et al. "Goodman & Gilman's The Pharmacological Basis of Therapeutics" (9th ed, 1996) p. 51 and 57-58.*
CAS STN Registry: structures for amantadine and acyclovir; serotonin and melatonin, p. 1-4.*
The Merck Index, Twelfth Edition, 1996, THER-17.*
Boman et al., "Cell-free Immunity in Cecropia", Eur. J. Biochem. (1991), 201, 23-31.

(Continued)

*Primary Examiner*—Sreeni Padmanabhan
*Assistant Examiner*—Abigail M. Cotton
(74) *Attorney, Agent, or Firm*—McDonnell Boehnen Hulbert & Berghoff LLP

(57) ABSTRACT

This invention herein describes a method of facilitating the entry of drugs into cells and tissues at physiologically protected sites at pharmacokinetically useful levels and also a method of targeting drugs to physiologically protected sites in vivo. Also provided are drug conjugates with an amino acid or derivative thereof for facilitating such targeted drug delivery. The conjugates and methods of this invention provide an advance over other drug targeting methods known in the prior art, because the invention provides drug concentrations in such physiologically protected sites that can reach therapeutically-effective levels after administration of systemic levels much lower than are currently administered to achieve a therapeutic dose. This technology is appropriate for use with psychotropic, neurotropic, neurological, antibiotic, antibacterial, antimycotic, antiviral, antiproliferative or antineoplastic drugs, agents and conjugates, for rapid and efficient introduction of such agents across, e.g., the blood-brain barrier. Further, the invention provides means for retention and prolonged enzymatic release of such drugs, agents and conjugates comprising the conjugates of the invention, in the brain and central nervous system and other physiologically-protected sites.

7 Claims, 1 Drawing Sheet

OTHER PUBLICATIONS

Lee et al., "Antibacterial peptides from pig intestine: Isolation of a Mammalian cecropin", Proc. Natl. Acad. Sci. 1989, 86:9159-9162.

Lehrer et al., "Defensins: Edogenous Antibiotic Peptides of Animal Cells", Cell, (1991), 64:229-230.

Zasloff et al., "Magainins, a class of Antimicrobial peptides from Xenopus skin: Isolation, characterization of two active forms, and partial cDNA sequence of a precursor", Proc. Natl. Acad. Sci. (1997) 84:5449-5453.

* cited by examiner

MELATONIN

LEVADOPA

LEVADOPA-MELATONIN CONJUGATE 1: ESTERASE CLEAVAGE
RELEASES LEVADOPA AND DEMETHOXYLATED MELATONIN

LEVADOPA-MELATONIN CONJUGATE 2: ESTERASE CLEAVAGE
RELEASES LEVADOPA AND N-FORMYLMELATONIN

COVALENT CONJUGATES OF BIOLOGICALLY-ACTIVE COMPOUNDS WITH AMINO ACIDS AND AMINO ACID DERIVATIVES FOR TARGETING TO PHYSIOLOGICALLY-PROTECTED SITES

BACKGROUND OF THE INVENTION

1. Field of the Invention

This invention is related to specific targeting of biologically-active compounds to specific cells, tissues and organs in vivo. The invention specifically provides conjugates of biologically-active compounds and methods of effecting the uptake and accumulation of biologically active compounds into organs, tissues and cells, particularly at physiologically protected sites, at pharmacokinetically useful levels. The conjugates of this invention permit drug concentrations to be achieved, especially at physiologically protected sites, at levels at which such compounds are therapeutically effective after administration of systemic levels much lower than currently attainable otherwise. This technology is appropriate for rapid and efficient introduction of a variety of biologically active compounds, particularly antibacterial, antibiotic, antiviral, antimycotic, antiproliferative and antineoplastic drugs and agents, and neurotropic, psychotropic and anticonvulsant drugs and agents, to biologically protected sites, for example across the blood-brain barrier.

2. Background of the Invention

A major goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. One common example of the need for such specificity is in the field of neurologic agent therapy for the treatment of diseases of the central nervous system, particularly the brain, which is protected by a layer of endothelial cells and other structures collectively known as the blood-brain barrier. In the pharmacological and neurologic arts, it is well-recognized that the inability to deliver effective amounts of neurotropic, psychotropic and anticonvulsant drugs and agents across the blood-brain barrier severely limits the therapeutic efficacy of such pharmaceutical compounds and can prevent treatment of neurologic disease. In addition, the use of even effective neurologic agents is further limited by systemic toxicity resulting from the high systemic concentrations that must be administered to achieve a therapeutic concentration of such agents in the brain, central nervous system and other neurological structures. Similar considerations apply in other organs and tissues in mammals that are protected by such blood-related barriers, such as the testes.

Another example of the need for such specificity is for introducing or administering antimicrobial, antiviral and antiproliferative and antineoplastic compounds, drugs or agents, into physiologically-protected reservoirs in an animal such as the brain, central nervous system, eyes and testes. Avoiding general systemic side-effects is particularly important in administering antimicrobial, antiviral and antiproliferative and antineoplastic compounds, drugs or agents targeted to such physiologically-protected sites, since achieving clinically useful concentrations of said compounds at these sites has frequently required administration of high systemic dosages which are associated with greater-than-acceptable levels of systemic toxicity.

It is desirable to increase the efficiency and specificity of administration of a therapeutic agent to the cells of the relevant tissues protected by physiological barriers (e.g., the blood-brain barrier) in a variety of pathological states. Psychotropic, neurological and neurotropic agents and antimicrobial, antiviral and antiproliferative and antineoplastic compounds typically have systemic effects, including renal and hepatotoxicity, hematopoietic suppression, teratogenic capacity, partitioning into breast milk and other pleiotropic cytotoxic effects that damage or otherwise deleteriously impact on uninvolved cells and tissues. Thus, an efficient delivery system which would enable the delivery of such drugs specifically to cells and tissues in such physiologically protected sites would increase the efficacy of treatment and reduce the associated "side effects" of such drug treatments, and also serve to reduce morbidity and mortality associated with clinical administration of such drugs. In addition, specific targeting of specific organs, tissues or cells wherein a biologically active compound preferentially accumulates in a specific organ, tissue or cell and does not generally or systemically accumulate in organs, tissues or cells in a body is desirable.

An additional challenge in designing an appropriate drug delivery scheme is to include within the drug conjugate a functionality that could either accelerate or reduce the rate at which the drug is released upon arrival at the desired site. Such a functionality would be especially valuable if it allowed differential rates of drug release, or specific release only at the appropriate drug target site comprising a specific organ, tissue or cell in a body.

Drug Targeting

Numerous methods for enhancing the biological activity and the specificity of drug action have been proposed or attempted (see, for example, Kreeger, 1996, *The Scientist*, Sep. 16, 1996, p. 6). To date, however, efficient or specific drug delivery remains to be predictably achieved.

U.S. Pat. No. 5,017,566, issued May 21, 1991 to Bodor discloses β- and γ-cyclodextrin derivatives comprising inclusion complexes of lipoidal forms of dihydropyridine redox targeting moieties.

U.S. Pat. No. 5,023,252, issued Jun. 11, 1991 to Hseih disclose the use of pharmaceutical compositions comprising a neurologically active drug and a compound for facilitating transport of said drug across the blood-brain barrier including a macrocyclic ester, diester, amide, diamide, amidine, diamidine, thioester, dithioester, thioamide, ketone or lactone.

U.S. Pat. No. 5,024,998, issued Jun. 18, 1991 to Bodor discloses parenteral solutions of aqueous-insoluble drugs with β- and γ-cyclodextrin derivatives.

U.S. Pat. No. 5,039,794, issued Aug. 13, 1991 to Wier et al. disclose the use of a metastatic tumor-derived egress factor for facilitating the transport of compounds across the blood-brain barrier.

U.S. Pat. No. 5,112,863, issued May 12, 1992 to Hashimoto et al. disclose the use of N-acyl amino acid derivatives as antipsychotic drugs for delivery across the blood-brain barrier.

U.S. Pat. No. 5,124,146, issued Jun. 23, 1992 to Neuwelt disclose a method for delivery of therapeutic agents across the blood-brain barrier at sites of increase permeability associated with brain lesions.

U.S. Pat. No. 5,149,794, issued Sep. 22, 1992 to Yatvin et al. discloses lipid conjugates with antineoplastic and antiviral drugs.

U.S. Pat. No. 5,153,179, issued Oct. 6, 1992 to Eibl discloses acylated glycerol and derivatives for use in a medicament for improved penetration of cell membranes.

U.S. Pat. No. 5,177,064, issued Jan. 5, 1993 to Bodor discloses the use of lipoidal phosphonate derivatives of nucleoside antiviral agents for delivery across the blood-brain barrier.

U.S. Pat. No. 5,223,263, issued Jun. 29, 1993 to Hostetler et al. discloses conjugates between antiviral nucleoside analogues and polar lipids, including phospholipids and ceramide.

U.S. Pat. No. 5,254,342, issued Oct. 19, 1993 to Shen et al. disclose receptor-mediated transcytosis of the blood-brain barrier using the transferrin receptor in combination with pharmaceutical compounds that enhance or accelerate this process.

U.S. Pat. No. 5,256,641, issued Oct. 26, 1993 to Yatvin et al. discloses lipid conjugates with antigenic peptides.

U.S. Pat. No. 5,258,402, issued Nov. 2, 1993 to Maryanoff discloses treatment of epilepsy with imidate derivatives of anticonvulsive sulfamate.

U.S. Pat. No. 5,270,312, issued Dec. 14, 1993 to Glase et al. discloses substituted piperazines as central nervous system agents.

U.S. Pat. No. 5,284,876, issued Feb. 8, 1994 to Shashoua et al., disclose fatty acid conjugates of dopanergic drugs for tardive dyskinesia.

U.S. Pat. No. 5,389,623, issued Feb. 14, 1995 to Bodor discloses the use of lipoidal dihydropyridine derivatives of anti-inflammatory steroids or steroid sex hormones for delivery across the blood-brain barrier.

U.S. Pat. No. 5,405,834, issued Apr. 11, 1995 to Bundgaard et al. discloses prodrug derivatives of thyrotropin releasing hormone.

U.S. Pat. No. 5,413,996, issued May 9, 1995 to Bodor disclose acyloxyalkyl phosphonate conjugates of neurologically-active drugs for anionic sequestration of such drugs in brain tissue.

U.S. Pat. No. 5,434,137, issued Jul. 18, 1995 to Black disclose methods for the selective opening of abnormal brain tissue capillaries using bradykinin infused into the carotid artery.

U.S. Pat. No. 5,442,043, issued Aug. 15, 1995 to Fukuta et al. disclose a peptide conjugate between a peptide having a biological activity and incapable of crossing the blood-brain barrier and a peptide which exhibits no biological activity and is capable of passing the blood-brain barrier by receptor-mediated endocytosis.

U.S. Pat. No. 5,466,683, issued Nov. 14, 1995 to Sterling et al. disclose water soluble analogues of the anticonvulsant Tegretol® (carbamazepine) for the treatment of epilepsy.

U.S. Pat. No. 5,484,809, issued Jan. 16, 1996 to Hostetler et al. discloses taxol and taxol derivatives conjugated to phospholipids.

U.S. Pat. No. 5,484,911, issued Jan. 16, 1996 to Hong et al. disclose nucleoside analogues conjugates to lipid moieties.

U.S. Pat. No. 5,512,671, issued Apr. 30, 1996 to Piantadosi et al. disclose nucleoside analogues conjugates to lipid moieties.

U.S. Pat. No. 5,525,727, issued Jun. 11, 1996 to Bodor disclose compositions for differential uptake and retention in brain tissue comprising a conjugate of a narcotic analgesic and agonists and antagonists thereof with a lipoidal form of dihydropyridine that forms a redox salt upon uptake across the blood-brain barrier that prevents partitioning back to the systemic circulation thereafter.

U.S. Pat. No. 5,543,389, issued Aug. 6, 1996 to Yatvin et al. discloses salves and ointments for delivering antiproliferative compounds to skin.

U.S. Pat. No. 5,554,728, issued Sep. 10, 1996 to Basava et al. discloses therapeutic peptides conjugated to lipid moieties.

U.S. Pat. No. 5,563,257, issued Oct. 8, 1998 to Zilch et al. disclose nucleoside analogues conjugates to ether lipid moieties.

U.S. Pat. No. 5,580,571, issued Dec. 3, 1996 to Hostetler et al. discloses nucleoside analogues conjugated to phospholipids.

U.S. Pat. No. 5,696,097, issued Dec. 9, 1997 to Matsuda et al. disclose nucleoside analogues conjugates to lipid moieties.

U.S. Pat. No. 5,744,461, issued Apr. 28, 1998 to Hostetler et al. disclose nucleoside analogues conjugated to phosphonoacetic acid lipid derivatives.

U.S. Pat. No. 5,744,592, issued Apr. 28, 1998 to Hostetler et al. disclose nucleoside analogues conjugated to phospholipids.

U.S. Pat. No. 5,756,116, issued May 26, 1998 to Hostetler et al. discloses nucleoside analogues.

U.S. Pat. No. 5,756,711, issued May 26, 1998 to Zilch et al. disclose nucleoside analogues conjugates to lipid moieties.

U.S. Pat. No. 5,827,819, issued Oct. 27, 1998 to Yatvin et al. disclose use of polar lipid conjugates to facilitate delivery of neurologic drugs to tissues of the central nervous system across the blood brain barrier.

U.S. Pat. No. 5,827,831, issued Oct. 27, 1998 to Hostetler et al. discloses phospholipid-drug conjugates having enhanced gastrointestinal bioavailability.

International Patent Application Publication Number WO85/02342, published 6 Jun. 1985 for Max-Planck Institute discloses a drug composition comprising a glycerolipid or derivative thereof.

International Patent Application Publication Number WO89/02733, published April 1989 to Vical discloses conjugates between antiviral nucleoside analogues and polar lipids, including phospholipids and ceramide.

International Patent Application Publication Number WO89/11299, published Nov. 30, 1989 for State of Oregon disclose a chemical conjugate of an antibody with a an enzyme which is delivered specifically to a brain lesion site for activating a separately-administered neurologically-active prodrug.

International Patent Application Publication Number WO91/04014, published 4 Apr. 1991 for Synergen, Inc. disclose methods for delivering therapeutic and diagnostic agents across the blood-brain barrier by encapsulating said drugs in liposomes targeted to brain tissue using transport-specific receptor ligands or antibodies.

International Patent Application Publication Number WO91/04745, published 18 Apr. 1991 for Athena Neurosciences, Inc. disclose transport across the blood-brain barrier using cell adhesion molecules and fragments thereof to increase the permeability of tight junctions in vascular endothelium.

International Patent Application Publication Number WO91/14438, published 3 Oct. 1991 for Columbia University disclose the use of a modified, chimeric monoclonal antibody for facilitating transport of substances across the blood-brain barrier.

International Patent Application Publication Number WO94/01131, published 20 Jan. 1994 for Eukarion, Inc. disclose lipidized proteins, including antibodies.

International Patent Application Publication Number WO94/03424, published 17 Feb. 1994 for Ishikura et al. disclose the use of amino acid derivatives as drug conjugates for facilitating transport across the blood-brain barrier.

International Patent Application Publication Number WO94/06450, published 31 Mar. 1994 for the University of Florida disclose conjugates of neurologically-active drugs with a dihydropyridine-type redox targeting moiety and comprising an amino acid linkage and an aliphatic residue.

International Patent Application Publication Number WO94/02178, published 3 Feb. 1994 for the U.S. Government, Department of Health and Human Services discloses antibody-targeted liposomes for delivery across the blood-brain barrier.

International Patent Application Publication Number WO95/07092, published 16 Mar. 1995 for the University of Medicine and Dentistry of New Jersey disclose the use of drug-growth factor conjugates for delivering drugs across the blood-brain barrier.

International Patent Application Publication Number WO96/00537, published 11 Jan. 1996 for Southern Research Institute disclose polymeric microspheres as injectable drug-delivery vehicles for delivering bioactive agents to sites within the central nervous system.

International Patent Application Publication Number WO96/04001, published 15 Feb. 1996 for Molecular/Structural Biotechnologies, Inc. disclose omega-3-fatty acid conjugates of neurologically-active drugs for brain tissue delivery.

International Patent Application Publication Number WO96/22303, published 25 Jul. 1996 for the Commonwealth Scientific and Industrial Research Organization disclose fatty acid and glycerolipid conjugates of neurologically-active drugs for brain tissue delivery.

International Patent Application Publication Number WO98/03204, published 29 Jan. 1998 for State of Oregon discloses salves and ointments for delivering antiproliferative compounds to skin.

International Patent Application Publication Number WO98/17325, published 30 Apr. 1998 for Oregon Health Sciences University discloses lipid conjugates with neurologically-active drugs.

An additional challenge in designing an appropriate drug delivery scheme is to include within the drug conjugate a functionality that could either accelerate or reduce the rate at which the drug is released upon arrival at the desired site. Such a functionality would be especially valuable if it allowed differential rates of drug release, or specific release only at the appropriate drug target site.

There remains a need in the art for an effective means for the specific delivery of biologically-active compounds, particularly antibacterial, antibiotic, antiviral, antimycotic, antiproliferative and antineoplastic drugs and agents, and also particularly neurotropic, psychotropic and anticonvulsant drugs and agents, and further particularly antineoplastic and anticancer drugs and agents, to physiologically restricted or protected sites. Advantageous embodiments of such delivery means are formulated to efficiently deliver the biologically-active compound to a physiologically-protected site, such as the brain or central nervous system, while minimizing hepatic and renal uptake of the agent or hematopoietic insult resulting therefrom.

SUMMARY OF THE INVENTION

The present invention is directed to an improved method for delivering biologically-active compounds, particularly drugs including preferably antibacterial, antibiotic, antiviral, antimycotic, antiproliferative and antineoplastic drugs and agents, and neurotropic, psychotropic and anticonvulsant drugs and agents, to physiologically protected sites in an animal in vivo. This delivery system achieves specific delivery of such biologically-active compounds through conjugating the compounds with an amino acid or amino acid derivative that is specifically transported into said physiologically-protected sites. This invention has the specific advantage of facilitating the entry of such compounds into cells and tissues protected by such physiological barriers as the blood-brain barrier via an amino acid or amino acid derivative that is specifically transported into said physiologically-protected sites, achieving effective intracellular concentration of such compounds more efficiently and with more specificity than conventional delivery systems.

The invention provides compositions of matter comprising a biologically-active compound covalently linked to an amino acid or amino acid derivative that is specifically transported into a physiologically-protected site. Preferred embodiments also comprise a spacer molecule having two linker functional groups, wherein the spacer has a first end and a second end and wherein the amino acid or amino acid derivative is attached to the first end of the spacer through a first linker functional group and the biologically-active compound is attached to the second end of the spacer through a second linker functional group. In preferred embodiments, the biologically-active compound is a drug, most preferably an antibacterial, antibiotic, antiviral, antimycotic, antiproliferative or antineoplastic drug or agent, or a neurotropic, psychotropic or anticonvulsant drug or agent. Preferred amino acid or amino acid derivatives include but are not limited to hydroxytryptophan, serotonin, and most preferably melatonin. Pharmaceutical compositions comprising the drug/polar lipid conjugates of the invention are also provided.

The invention also provides compositions of matter comprising a biologically-active compound covalently linked to an amino acid or amino acid derivative via a spacer molecule wherein the spacer allows the biologically-active compound to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the biologically-active compound at an intracellular site. Other embodiments of the spacer facilitate the enzymatic release of the biologically-active compound at an intracellular site. In particularly preferred embodiments, the spacer functional group is hydrolyzed by an enzymatic activity found in brain tissue, including neuronal, glial and other brain cell types, preferably an esterase and most preferably an esterase having a differential expression and activity profile in the appropriate target cell type. In additional preferred embodiments, specific release of biologically-active compounds is achieved by enzymatic or chemical release of the biologically-active compound by extracellular cleavage of a cleavable linker moiety via an enzymatic activity specific for brain tissue, with resulting specific uptake of the released antibacterial, antibiotic, antiviral, antimycotic, antiproliferative or antineoplastic drug or agent, or a neurotropic, psychotropic or anticonvulsant drug or agent by the appropriate cell in said tissue.

In another embodiment of this aspect of the invention, the spacer molecule is a peptide of formula (amino acid)$_n$, wherein n is an integer between 2 and 25, preferably wherein the peptide comprises a polymer of one or more amino acids.

In other embodiments of the compositions of matter of the invention, the biologically-active compound of the invention has a first functional linker group, and an amino acid or amino acid derivative that is specifically transported into a physiologically-protected site having a second functional linker group, and the compound is covalently linked directly to the amino acid or amino acid derivative by a chemical bond between the first and second functional linker groups. In preferred embodiments, each of the first and second functional linker groups is a hydroxyl group, a primary or secondary amino group, a phosphate group or substituted derivatives thereof or a carboxylic acid group.

In another aspect of the invention is provided compositions of matter comprising a drug, most preferably an antibacterial, antibiotic, antiviral, antimycotic, antiproliferative or antineoplastic drug or agent, or a neurotropic, psychotropic or anticonvulsant drug or agent, covalently linked to an amino acid or amino acid derivative that is specifically transported into a physiologically-protected site. Preferred embodiments also comprise a spacer molecule having two linker functional groups, wherein the spacer has a first end and a second end and wherein the amino acid or amino acid derivative is attached to the first end of the spacer through a first linker functional group and the drug is attached to the second end of the spacer through a second linker functional group. Preferred embodiments of the invention are provided wherein the drug is an antibacterial, antibiotic, antiviral, antimycotic, antiproliferative or antineoplastic drug or agent, or a neurotropic, psychotropic or anticonvulsant drug or agent. Preferred amino acid or amino acid derivatives include but are not limited to hydroxytryptophan, serotonin, and most preferably melatonin. Pharmaceutical compositions comprising the conjugates of the invention are also provided.

The invention also provides compositions of matter comprising antibacterial, antibiotic, antiviral, antimycotic, antiproliferative or antineoplastic drug or agent, or a neurotropic, psychotropic or anticonvulsant drug or agent, covalently linked to an amino acid or amino acid derivative via a spacer molecule, wherein the spacer allows the drug to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of antibacterial, antibiotic, antiviral, antimycotic, antiproliferative or antineoplastic drug or agent, or a neurotropic, psychotropic or anticonvulsant drug or agent at an intracellular site. Other embodiments of the spacer facilitate the enzymatic release of the antibacterial, antibiotic, antiviral, antimycotic, antiproliferative or antineoplastic drug or agent, or a neurotropic, psychotropic or anticonvulsant drug or agent of the invention at an intracellular site. In particularly preferred embodiments, the spacer functional group is hydrolyzed by an enzymatic activity found in a physiologically-protected site, such as the brain and central nervous system and more particularly including neuronal, glial and other brain cell types, wherein said enzymatic activity is preferably an esterase and most preferably an esterase having a differential expression and activity profile in different tissue cell types. In additional preferred embodiments, specific release of the antibacterial, antibiotic, antiviral, antimycotic, antiproliferative or antineoplastic drug or agent, or a neurotropic, psychotropic or anticonvulsant drug or agent of the invention is achieved by enzymatic or chemical release of these drugs by extracellular cleavage of a cleavable linker moiety via an enzymatic activity specific for, for example, brain tissue, followed by specific uptake of the released antibacterial, antibiotic, antiviral, antimycotic, antiproliferative or antineoplastic drug or agent, or a neurotropic, psychotropic or anticonvulsant drug or agent by the appropriate cell in said tissue.

In another embodiment of this aspect of the invention, the spacer molecule is a peptide of formula (amino acid)$_n$, wherein n is an integer between 2 and 25, preferably wherein the peptide comprises a polymer of one or more amino acids.

In still further embodiments of the compositions of matter of the invention are provided antibacterial, antibiotic, antiviral, antimycotic, antiproliferative or antineoplastic drug or agent, or a neurotropic, psychotropic or anticonvulsant drug or agent having a first functional linker group, and an amino acid or amino acid derivative having a second functional linker group, wherein the drug is covalently linked directly to the polar lipid carrier by a chemical bond between the first and second functional linker groups. In preferred embodiments, each of the first and second functional linker groups is a hydroxyl group, a primary or secondary amino group, a phosphate group or substituted derivatives thereof or a carboxylic acid group. Preferred amino acid or amino acid derivatives include but are not limited to hydroxytryptophan, serotonin, and most preferably melatonin. Pharmaceutical compositions comprising the conjugates of the invention are also provided.

As disclosed herein, the invention comprehends conjugates wherein the amino acid or amino acid derivative is specifically and selectively transported across certain physiological barriers to protected tissue sites, thereby facilitating delivery of drugs and other pharmaceutical agents to such physiologically restricted or protected sites. In embodiments comprising a spacer moiety, the spacer component of the conjugates of the invention will preferably act to specifically release the drug from the amino acid or derivative at the target site; prevent the non-specific release from the drug from the amino acid or derivative in the systemic circulation or in hepatic, renal or other inappropriate cells, tissue or organs; target the conjugate to a specific cell or cell type within the protected tissue; prevent interaction and/or uptake of the drug by hematopoietic, ocular, hepatic or renal tissues; or perform other functions to maximize the effectiveness of the drug.

This type of conjugate has numerous advantages. The conjugates of the invention provide delivery of a variety of antibacterial, antibiotic, antiviral, antimycotic, antiproliferative or antineoplastic drug or agent, or a neurotropic, psychotropic or anticonvulsant drug or agent to physiologically restricted or protected sites in vivo at concentrations and pharmacokinetic rates not heretofore attainable. A benefit of this advantage is the achievement of therapeutic indices of agents in such protected sites whereby the agent is useful for achieving a desired therapeutic goal. Another benefit is decreased hepatic toxicity, hematopoietic suppression (such as thrombocytopenia, leukopenia, aplastic anemia, leukocytosis, eosinophilia, pancytopenia, agranulocytosis), reduced systemic metabolism, degradation and toxicity, reduced hepatic clearance, reduced systemic adverse drug interactions, and generally reduced side effects due to the achievement of a lower, therapeutically-effective dose as the result of surmounting the physiological barrier. These biological effects can also result in simplified dosage schedules, particularly for drugs with short systemic half-lives.

In particular, felicitous design of the psychotropic, neurotropic/neurological drug/spacer/amino acid conjugate can provide an in vivo reservoir of time-dependent drug release in the physiologically protected tissue, resulting in specific delivery of therapeutic amounts to such tissues using a reduced dosage regime to minimize non-specific, systemic and deleterious side effects. In such formulations, the amount and activity of the antibacterial, antibiotic, antiviral, antimycotic, antiproliferative or antineoplastic drug or agent, or a neurotropic, psychotropic or anticonvulsant drug or agent can be modulated by release via cleavage, preferably hydrolytic cleavage, of the spacer moiety, most preferably by an enzymatic activity in the protected tissue (e.g., brain) that has a differential pattern of expression or activity in different cell types in said tissue. The conjugates of the invention can also be combined with other drug delivery approaches to further increase specificity and to take advantage of useful advances in the art.

Specific preferred embodiments of the present invention will become evident from the following more detailed description of certain preferred embodiments and the claims.

DETAILED DESCRIPTION OF THE PREFERRED EMBODIMENTS

Figure 1:
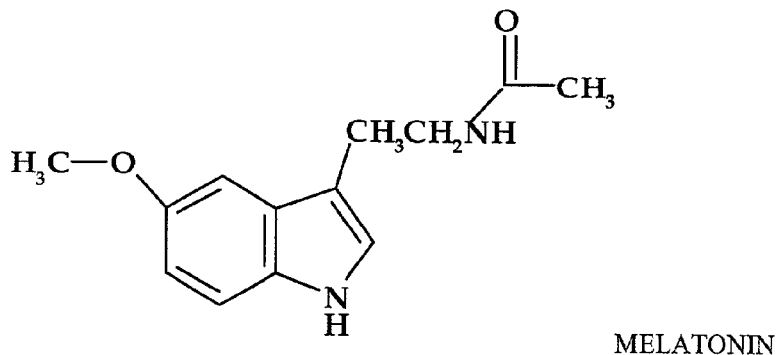
FIG. 1 illustrates two conjugates of the invention between leva-dopa and melatonin. These conjugates are cleaved by esterases expressed in tissues in biologically-protected sites.
Figure 1:
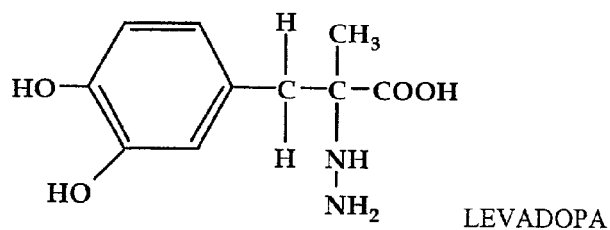
Figure 1:
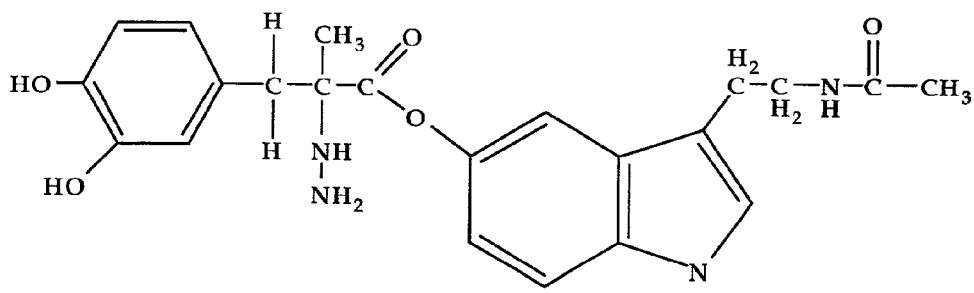
Figure 1:
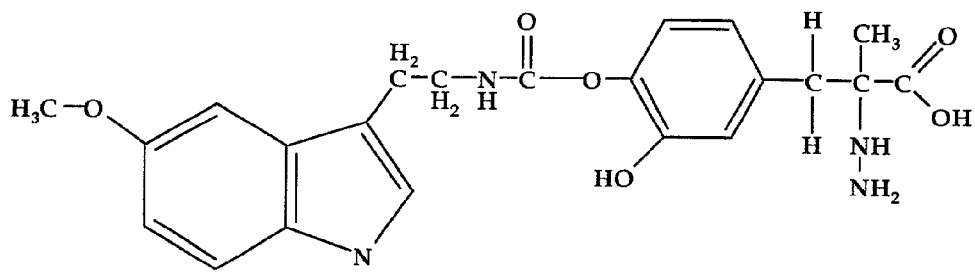

The present invention provides compositions of matter and methods for facilitating the entry into cells of biologically-active compounds. For the purposes of this invention, the term "biologically-active compound" is intended to encompass all naturally-occurring or synthetic compounds capable of eliciting a biological response or having an effect, either beneficial or cytotoxic, on biological systems, particularly cells and cellular organelles. These compounds are intended to include but are not limited to all varieties of drugs, particularly antibacterial, antibiotic, antiviral, antimycotic, antiproliferative and antineoplastic drugs and agents, and neurotropic, psychotropic and anticonvulsant drugs or agents.

As used herein the terms "psychotropic, neurotropic and neurologically-acting drugs and agents" are intended to include any drug, agent or compound having a neurological, neurotropic, or psychotropic effect in an animal, preferably a human. These terms are intended to encompass antiinflammatory agents, corticosteroids, sedatives, tranquilizers, narcotics, analgesics, anesthetics, anticonvulsive and antispasmodic agents, antiparkinsonian drugs, alkaloids, catecholamines, including dopamine analogues and derivatives, muscarinic receptor agonists and antagonists, cholinergic receptor agonists and antagonists, calcium channel blockers, γ-aminobutyric acid (GABA) receptor agonists, antagonists, and uptake inhibitors and enhancers; phenothiazines, thioxanthemes and related compounds; clozapine, haldoperidol, loxapine (Loxitane®), benzodiazapene antidepressants of the norepinephrine reuptake inhibitor type; monoamine oxidase inhibitors; antidepressants and antimanic agents, antioxidants such as carotenes, glutathione, N-acetylcysteine or other molecules that mitigate the effects of reactive oxygen species for the treatment of Alzheimer's disease, Parkinson's disease, or other neurodegenerative conditions such as ataxia telangiectasia and amyelolaterosclerosis (ALS); neuroregenerative agents; and agents for the treatment of ischemia and other vascular diseases of the central nervous system. Appropriate formulations and pharmaceutical compositions of the neurotropic/neurological/psychotropic drug/ amino acid or derivative conjugates of the invention will be apparent and within the skill of one of ordinary skill in this art to advantageously prepare in view of the instant disclosure.

As used herein the terms "antibiotic, antibacterial, antimycotic, antiviral, antiproliferative or antineoplastic drugs and agents" are intended to include any drug, agent or compound having an antibiotic, antibacterial, antimycotic, antiviral, antiproliferative or antineoplastic effect in an animal, preferably a human. In particular, the term "antimicrobial drug" will be understood to encompass said antibiotic, antibacterial, antimycotic, and antiviral compounds, as well as other compounds that have an antimicrobial effect (such as anti-plasmodial drugs).

For the purposes of this invention, the term "antimicrobial drug" is intended to encompass any pharmacological agent effective in inhibiting, attenuating, combating or overcoming infection of mammalian cells by a microbial pathogen in vivo or in vitro. Antimicrobial drugs as provided as components of the antimicrobial agents of the invention include but are not limited to penicillin and drugs of the penicillin family of antimicrobial drugs, including but not limited to penicillin-G, penicillin-V, phenethicillin, ampicillin, amoxacillin, cyclacillin, bacampicillin, hetacillin, cloxacillin, dicloxacillin, methicillin, nafcillin, oxacillin, azlocillin, carbenicillin, mezlocillin, piperacillin, ticaricillin, and imipenem; cephalosporin and drugs of the cephalosporin family, including but not limited to cefadroxil, cefazolin, caphalexin, cephalothin, cephapirin, cephradine, cefaclor, cefamandole, cefonicid, cefoxin, cefuroxime, ceforanide, cefotetan, cefinetazole, cefoperazone, cefotaxime, ceftizoxime, ceftizone, moxalactam, ceftazidime, and cefixime; aminoglycoside drugs and drugs of the aminoglycoside family, including but not limited to streptomycin, neomycin, kanamycin, gentamycin, tobramycin, amikacin, and netilmicin; macrolide and drugs of the macrolide family, exemplified by azithromycin, clarithromycin, roxithromycin, erythromycin, lincomycin, and clindamycin; tetracycline and drugs of the tetracycline family, for example, tetracycline, oxytetracycline, democlocyclin, methacyclin, doxycyclin, and minocyclin; quinoline and quinoline-like drugs, such as, for example, naladixic acid, cinoxacin, norfloxacin, ciprofloxacin, ofloxicin, enoxacin, and pefloxacin; antimicrobial peptides, including but not limited to polymixin B, colistin, and bacitracin, as well as other antimicrobial peptides such as defensins (Lehrer et al., 1991, *Cell* 64: 229–230), magainins (Zasloff, 1987, *Proc. Natl. Acad. Sci. USA* 84: 5449–5453), cecropins (Lee et al., 1989, *Proc. Natl. Acad. Sci. USA* 86: 9159–9162 and Boman et al., 1990, *Eur. J. Biochem.* 201: 23–31), and others, provided as naturally-occurring, chemically synthesized in vitro or produced as the result of engineering to make such peptides resistant to the action of pathogen-specific proteases and other deactivating enzymes; other antimicrobial drugs, including chloramphenicol, vancomycin, rifampicin, metronidazole, ethambutol, pyrazinamide, sulfonamides, isoniazid, and erythromycin.

Antiviral drugs, including but not limited to reverse transcriptase inhibitors, protease inhibitors, antiherpetics such as acyclovir and gancyclovir, azidothymidine, cytidine arabinoside, ribavirin, amantadine, iododeoxyuridine, foscamet, trifluoridine, methizazone, vidarabine and levanisole are also encompassed by this definition and are expressly included therein.

Antimycotic drugs provided by the invention and comprising the pharmaceutical compositions thereof include but are not limited to clotrimazole, nystatin, econazole and myconixole, ketoconazole, grisefulvin, ciclopixox, naftitine and other imidizole antimycotics.

Antiproliferative and antineoplastic agents provided by the invention and comprising the pharmaceutical compositions thereof include but are not limited to methotrexate, doxarubicin, daunarubicin, epipodophyllotoxins, 5-fluorouracil, tamoxifen, actinomycin D, vinblastine, vincristine, colchicine and taxol.

The invention also provides antibiotic drugs and agents wherein an antimicrobial agent is a toxin capable of specific cytotoxicity against the microbe, its host cell or both. The term "toxin" is intended to encompass any pharmacological agent capable of such toxicity, including for example ricin from jack bean, diphtheria toxin, and other naturally-occurring and man-made toxins.

The conjugates of the invention comprise the biologically-active compounds of the invention covalently linked to an amino acid or amino acid derivative that is specifically transported into a physiologically-protected site. Such compounds include but are not limited to 5-hydroxytryptophan, serotonin, and most preferably melatonin. The amino acids and derivative thereof encompassed by this definition include any amino acid, naturally-occurring or synthetic, and any derivative of an amino acid, including primary, secondary and tertiary amines, carboxylic acids, esters, amides, aldehydes, alcohols, ethers, and thiols, provided that any such derivative is preferentially partitioned into a physiologically protected site in vivo, including but not limited to eye, spleen, lung, testes and the central nervous system, most preferably the brain.

Appropriate formulations and pharmaceutical compositions of the conjugates of the invention comprising antibacterial, antibiotic, antiviral, antimycotic, antiproliferative and antineoplastic drugs or agents, or neurotropic, psychotropic or anticonvulsant drugs or agents will be apparent and within the skill of one of ordinary skill in this art to advantageously prepare in view of the instant disclosure. In preferred embodiments, said pharmaceutical compositions are provided for topical application, comprising appropriately chosen salves, ointments and emollients. In particularly preferred embodiments, said topical application is specifically adapted for administration to ocular tissues, comprising electrolytically balanced solutions for topical and direct administration to vertebrate, preferably mammalian and most preferably human eyes. In alternative formulations, the pharmaceutical composition comprises complexes formed for example with serum albumin, polyvinylpyrrolidone and other pharmaceutically acceptable carriers and excipients for parenteral administration, including but not limited to intravenous, intramuscular, and subcutaneous routes of administration. In yet alternative embodiments, the pharmaceutical compositions of the invention are provided to be orally bioavailable by administration in tablets, capsules, elixirs, gums, and other formulations comprising excipients adapted for transit of the conjugates of the invention through the gastrointestinal tract. Oral and parenteral routes of administration are preferred.

In preferred embodiments, the conjugates are provided wherein the biologically active compound is in a form having reduced, inhibited, or essentially no biological activity and wherein this form of the compound is capable of being converted by chemical or enzymatic means, most preferably in vivo, into a form having a desired biological activity; when the biologically active compound is a drug, this form of the drug is commonly termed a "prodrug." Embodiments of such prodrugs useful in the present invention include prodrugs that can be converted by chemical or enzymatic means in a targeted organ, tissue or cell in an animal. In preferred embodiments, said prodrugs are converted into a form having a desired biological activity in an organ or tissue extracellularly, i.e. within the physical and anatomically-recognized province of the organ or tissue but not within any particular cell in the organ or tissue. In such embodiments, the activated prodrug is then capable of having the desired biological activity without entry into any particular cell comprising said organ or tissue. In alternative embodiments, the activated prodrug is then capable of entering a cell comprising said organ or tissue and having the desired biological activity thereof. In additional preferred embodiments, the prodrug is only converted into the active form after entry into a particular cell or cell type comprising said organ or tissue.

As used herein, the terms "chemical or enzymatic means" is intended to encompass chemical conditions (including but not limited to salt or other electrolyte concentration, metabolite concentration, pH, osmolality, osmolarity, dielectric constant, temperature, pressure, or chemical catalyst concentration) or presence of enzymatic activity (including but not limited to esterases, amidases, peptidases, nucleases, peroxidases, lipases, or redox proteins) in an organ, tissue or cell, most preferably in a physiologically-protected site in an animal, most preferably a human. It will be understood that the choice of spacer moiety comprising any particular embodiment of the pharmaceutical compositions or compositions of matter of the invention, and particularly the choice of said linker functional groups comprising said spacer moieties, is chosen to match the chemical or enzymatic means present in the organ, tissue or cell targeted by said composition.

The compositions of matter and pharmaceutical compositions of the invention may further comprise a spacer moiety comprising a first end and a second end, each end of the spacer having a functional linking group. For the purposes of this invention, the term "spacer" or "spacer moiety" is intended to encompass any chemical entity that links a biologically-active compound and an amino acid or derivative thereof according to the invention. Such spacer moieties may be designed to promote or effect the delivery to or accumulation at specific organs, tissues or cells, or to promote, influence, modulate or regulate the release of the biologically-active compound at the desired target site. Such spacers may facilitate enzymatic release at specific organs, tissues and cell, preferably at extracellular sites therein; more preferably, said spacers inhibit enzymatic, hydrolytic or other release systemically in an animal. Spacer groups, as described herein, include, but are not limited to aminohexanoic acid, adipic acid, and other bifunctional organic acids; peptides including homopolymers such as polyglycine; substituted fatty acids; carbohydrate moieties including mono-, di- and other saccharides; oligonucleotides; polyamides, polyethylenes, and short functionalized polymers having a carbon backbone which is from one to about twelve carbon molecules in length. Particularly preferred embodiments of such spacer moieties comprise peptides of formula (amino acid)$_n$, wherein n is an integer between 2 and 25 and the peptide is a polymer of one or more amino acids.

The term "linker functional group" is defined herein as any functional group for covalently binding the amino acid or derivative thereof or biologically-active agent to the spacer group. These groups can be designated either "weak" or "strong" based on the stability of the covalent bond that the linker functional group will form between the spacer and either the amino acid or derivative thereof or the biologically-active compound. The weak functionalities include, but are not limited to phosphoramide, phosphoester, carbonate, amide, carboxyl-phosphoryl anhydride, thioester and most preferably ester. The strong functionalities include, but are not limited to ether, thioether, amine, amide and most preferably ester. The use of a strong linker functional group between the spacer group and the biologically-active compound will tend to decrease the rate at which the compound will be released at the target site, whereas the use of a weak linker functional group between the spacer group and the compound may act to increase the release rate of the compound at the target site. Enzymatic release is, of course, also possible, but such enzyme-mediated modes of release will not necessarily be correlated with bond strength in such embodiments of the invention. Spacer moieties comprising enzyme active site recognition groups, such as spacer groups comprising peptides having proteolytic cleavage sites therein, are envisioned as being within the scope of the present invention. Specifically, such specifically-cleavable peptides are preferably prepared so as to be recognized by enzymes present in particular organs or tissues such as brain and other physiologically restricted or protected sites in vivo, so that the drug is preferentially liberated from the polar lipid conjugate at appropriate drug delivery sites. An illustrative example of such a specifically-cleavable peptide is a portion of the proopiomelanocortin family of peptides, which are cleaved in mammalian brain tissue to release a variety of peptides hormones and effector molecules, such as the enkephalins. Those of ordinary skill in the art will recognize other beneficial and advantageous specifically-cleavable peptides. The linker functional groups are selected to inhibit or prevent cleavage of the covalent linkage between the spacer and the biologically active compound, or between the spacer and the polar lipid carrier, at a site other than the specific site to which the conjugate is targeted.

The conjugates of the invention are preferably provided comprised of spacer moieties that impart differential release properties on the conjugates related to differential expression or activity of enzymatic activities in physiologically restricted or protected sites in comparison with such activities in systemic circulation or in inappropriate targets, such as hepatic, renal or hematopoietic tissues. Differential release is also provided in certain embodiments in specific cell types comprising such physiologically protected tissues.

In particularly preferred embodiments of the present invention are provided conjugates comprising neurotropic, psychotropic and anticonvulsant drugs or agents for specific delivery to brain tissue for the alleviation or amelioration of pathological disease states in the brain. Thus, the present invention provides methods and compositions of matter for facilitating the transit of such conjugates of antibacterial, antibiotic, antiviral, antimycotic, antiproliferative and antineoplastic drugs and agents, and neurotropic, psychotropic and anticonvulsant drugs or agents across the blood-brain barrier and into targeted regions of the brain, for the treatment of animal, preferably human, diseases and pathological conditions. Among the most common such diseases and conditions are Alzheimer's disease, Parkinson's disease, epilepsy and other seizure disorders (such as petit mal, grand mal, tonic-clonic seizure disorder, parietal complex seizure, and psychomotor seizures), migraine, neurodegenerative conditions such as ataxia telangiectasia and ALS, Lennox-Gastaut syndrome, neuropathy such as trigeminal neuralgia, diabetic neuropathy, shingles, and psychological disorders, including bipolar disorder, explosive aggression, depression and agitation associated with elderly dementia.

The invention provides conjugates comprising psychotropic, neurotropic and neurological drugs, agents and compounds including but not limited to L-dopa, hydroxytryptamine and metabolites thereof; amantadine, benztropine, bromocryptine, diphenhydramine, levadopa (a particularly preferred embodiment) and combinations thereof (e.g., with carbidopa as provided as Sinemet®); pergolid, trihexphenidyl, ethosuximide, valproic acid, carbamazepine (e.g., Tegretol®) and, in a particularly preferred embodiment, the 10- or 11-hydroxy analogues of carbamazepine; primidone, gabapentin in a particularly preferred embodiment; lamotrigine in a particularly preferred embodiment; felbamate, paramethadione and trimethadione; phenothiazines, thioxanthemes and related compounds; clozapine, haldoperidol, loxapine (Loxitane®), benzodiazapene antidepressants of the norepinephrine reuptake inhibitor type; monoamine oxidase inhibitors, and antioxidants such as carotenes, glutathione and N-acetylcysteine.

The invention provides conjugates comprising antibiotic, antibacterial, antimycotic, antiviral, antiproliferative or antineoplastic drugs, agents and compounds including but not limited to methotrexate, azidothymidine, dideoxyinosine, dideoxycytosine, acyclovir, or gancyclovir.

The invention specifically provides methods for preparing and administering such psychotropic, neurotropic, neurological, antibiotic, antibacterial, antimycotic, antiviral, antiproliferative or antineoplastic drugs, agent and compounds for use in treating pathological conditions in vivo.

The invention also provides embodiments of the conjugates disclosed herein as pharmaceutical compositions. The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries that facilitate processing of the active conjugates into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

For injection, the conjugates of the invention can be formulated in appropriate aqueous solutions, such as physiologically compatible buffers such as Hanks' solution, Ringer's solution, or physiological saline buffer. For transmucosal and transcutaneous administration, penetrants appropriate to the barrier to be permeated are used in the formulation. Such penetrants are generally known in the art.

For oral administration, the conjugates can be formulated readily by combining the active conjugates with pharmaceutically acceptable carriers well known in the art. Such carriers enable the conjugates of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active conjugates can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the conjugates for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The conjugates can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active conjugates in water-soluble form. Additionally, suspensions of the active conjugates can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the conjugates to allow for the preparation of highly concentrated solutions. Alternatively, the active ingredient can be in powder form for constitution with a suitable vehicle, e.g., sterile pyrogen-free water, before use. The conjugates can also be formulated in rectal compositions such as suppositories or retention enemas, e.g., containing conventional suppository bases such as cocoa butter or other glycerides.

In addition to the formulations described previously, the conjugates can also be formulated as a depot preparation. Such long acting formulations can be administered by implantation (for example subcutaneously or intramuscularly) or by intramuscular injection. Thus, for example, the conjugates can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic conjugates of the invention is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic conjugates well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems for hydrophobic pharmaceutical conjugates can be employed. Liposomes and emulsions are well known examples of delivery vehicles or carriers for hydrophobic drugs. Certain organic solvents such as dimethylsulfoxide also can be employed, although usually at the cost of greater toxicity. Additionally, the conjugates can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the conjugates for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The conjugates of the invention can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, HOOC—$(CH_2)_n$—$CH_3$ where n is 0–4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical compositions of the conjugates of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the conjugates in a local rather than systemic manner, for example, via injection of the compound directly into a specific tissue, often in a depot or sustained release formulation.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any conjugate species used in the method of the invention, the therapeutically effective dose can be estimated initially in vitro, for example, from cell culture assays, as disclosed herein. For example, a dose can be formulated in animal models to achieve a circulating concentration range that includes the EC50 (effective dose for 50% increase) as determined in cell culture. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Toxicity and therapeutic efficacy of such conjugates can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Conjugates that exhibit high therapeutic indices are preferred. The data obtained from these cell culture assays and animal studies can be used in formulating a range of dosage for use in humans. The dosage of such conjugates lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

In particularly preferred embodiments of the present invention are provided conjugates comprising antibiotic, antibacterial, antimycotic, antiviral, antiproliferative or antineoplastic drugs for specific delivery to or accumulation in specific organs, tissues and cells in an animal. In particularly preferred embodiments, the conjugates are targeted to the central nervous system, most preferably brain tissue, for the alleviation or amelioration of pathological disease states therein. In such embodiments of the invention are provided methods and conjugates for facilitating the transit of such conjugates of antibiotic, antibacterial, antimycotic, antiviral, antiproliferative or antineoplastic drugs, agents and conjugates across the blood-brain barrier and into targeted regions of the brain and other physiologically protected sites, for the treatment of animal, preferably human, diseases and pathological conditions. Among the most common such diseases and conditions are acquired immune deficiency syndrome, neuroblastoma, glioma, astrocytoma, meningioma, sarcoma, metastatic melanoma, metastatic adenocarcinoma, lung tumors such as adenocarcinoma, small cell carcinoma, and other tumors of the lung; tuberculosis; bronchitis; emphysema; pneumonia; cystic fibrosis; Gaucher's disease; and other diseases and disorders of lung or spleen tissue; syphilis, encephalitis, meningitis, nocardiosis, abscess, coccidiodomycosis, cryptococcosis, subdural empyema, extrapulmonary tuberculosis, leptospirosis, toxoplasmosis, trichinosis, trypanosomiasis, mycoplasma infection, herpetic encephalitis, and schistosomiasis.

Animals to be treated with the inventive conjugates using the methods of the invention are intended to include all vertebrate animals, preferably domesticated animals, such as cattle, horses, goats, sheep, fowl, fish, household pets, and others, as well as wild animals, and most preferably humans.

The following Examples illustrate certain aspects of the above-described method and advantageous results. The following examples are shown by way of illustration and not by way of limitation.

EXAMPLE 1

Conjugates between melatonin and melatonin derivatives with biologically-active compounds were prepared as follows.

As a first step, melatonin is converted to modifiable melatonin derivatives, illustrated herein by the indole N—OH and indole N-formoxy ester derivatives.

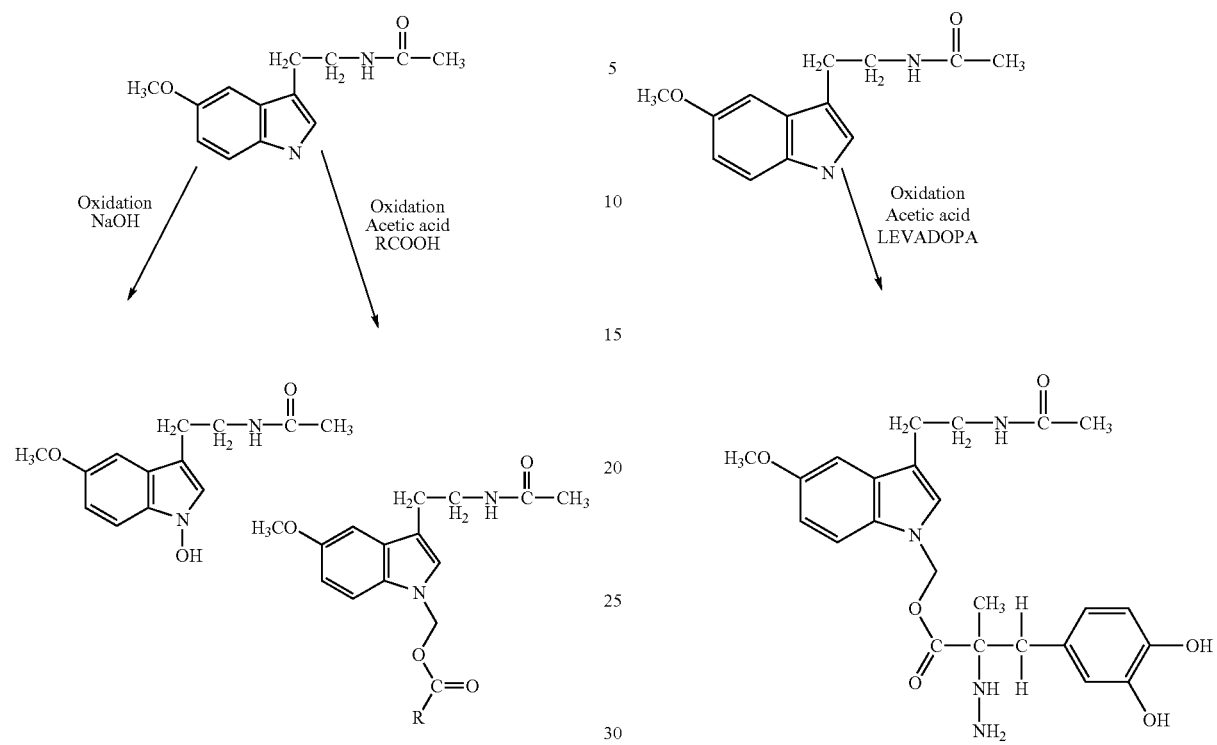

Alternatively, serotonin is converted to demethoxylated melatonin (N-acetyl serotonin).

SEROTONIN

ACETIC ACID
ACETIC ANHYDRIDE
─────────────────
Aq NaOH

N-acetylserotonin

Levadopa conjugates as shown in FIG. 1 can be prepared from either of the indole N melatonin derivatives. In the following synthetic scheme, all hydroxyls and hydrazine protons of levadopa are protected by reaction with trimethyl silyl chloride to form TMS adducts. These adducts are removed after reaction by treatment in dilute acid.

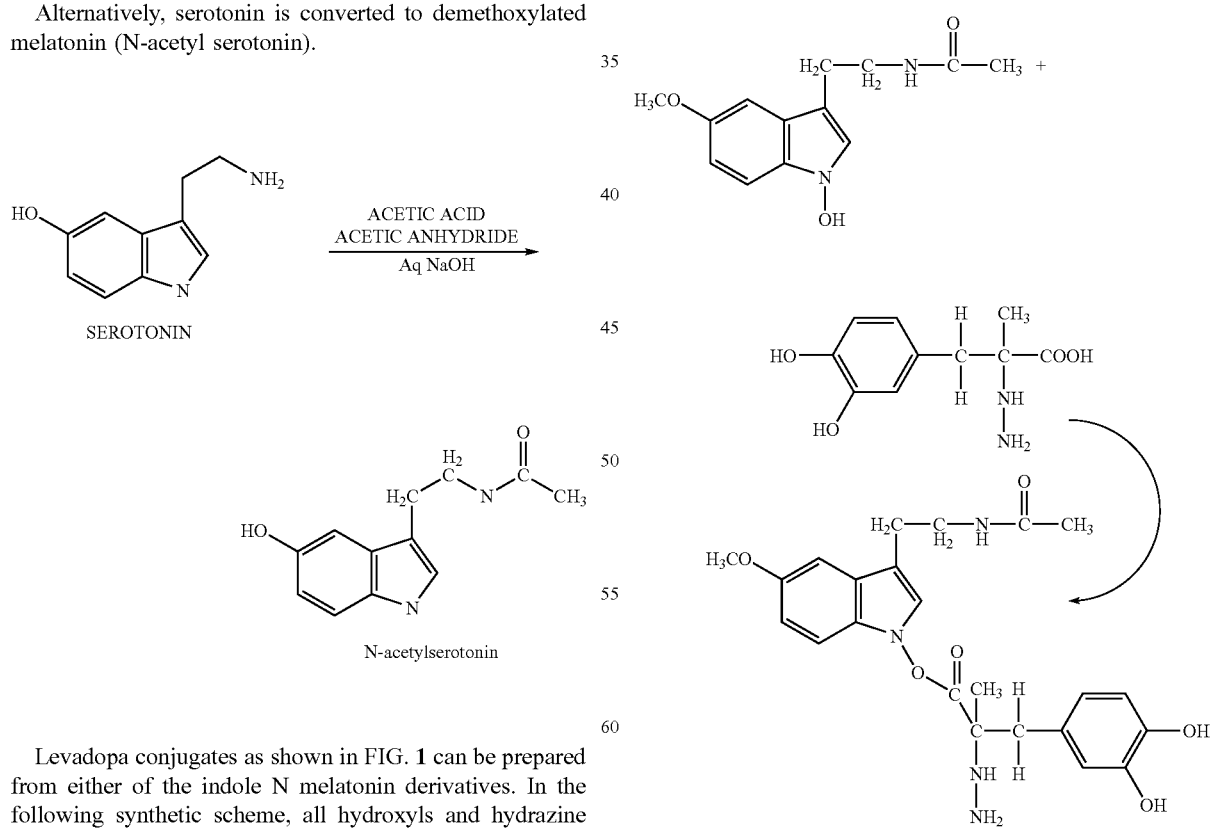

or the ring hydroxylated product:

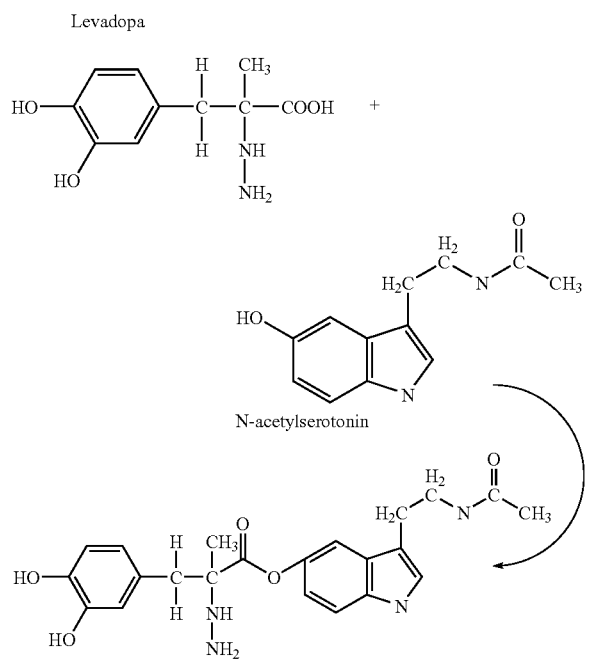

Synthesis of N-Hydroxy Melatonin

The synthesis of N-hydroxy melatonin uses conditions described by Bilaski and Ganem (1983, *Synthesis*, p.537). Briefly, to a 100 mL round-bottomed flask is added 1 g (4.3 mmol) melatonin, 50 mL of 25% water in isopropyl alcohol, and 2.84 g (20 mmol) disodium hydrogen phosphate. The solution was cooled to 0° C. under argon, followed by the slow addition of 1.56 g (6.5 mmol) benzoyl peroxide over 4 hrs. After stirring at 0° C. for 20 hr the reaction was quenched by the addition of 10 wt % sodium thiosulfite, followed by 5×50 mL washes with methylene chloride. The methylene chloride fractions were combined and solvent removed under reduced pressure. The product was recrystallized from benzene/chloroform to yield 266 mg (1.07 mmol) of N-hydroxy melatonin.

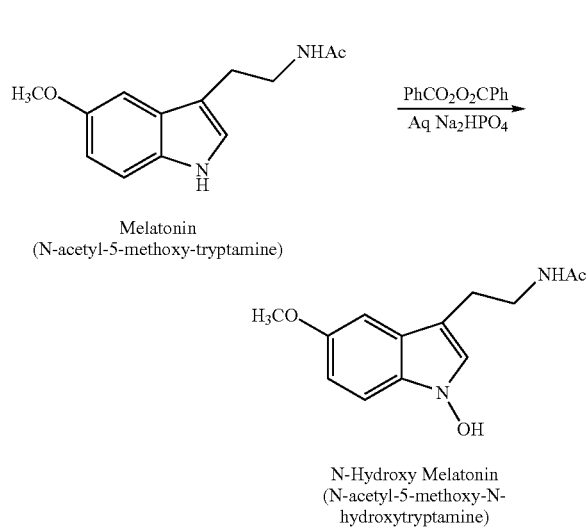

Synthesis of N-Alkoxymethyl Melatonin

To a 100 mL round-bottomed flask is added 1 g (4.3 mmol) melatonin, 50 mL of methylene chloride, and 2.02 g (20 mmol) diisopropyl amine. The solution was cooled to 0° C. under argon, followed by the slow addition of 0.64 g (4.3 mmol) of the chloromethyl ester of 3,3,3-chlorodimethyl acrylate over 1 hr. (Chloromethyl ester of 3,3-dimethyl acrylate is prepared by an analogous procedure for the synthesis of benzyl chloromethyl ester set forth in *Organic Synthesis Col* III: 101.) After stirring at 0° C. for 20 hr the reaction was quenched by the addition of 10 mL of 4.0 M hydrochloric acid and 2×10 mL of brine, followed by drying over anhydrous sodium sulfate. The solution was filtered, concentrated and purified by recrystallization from benzene to yield 1.3 g (3.8 mmol) of (N-methyl ester of 3,3-dimethyl acrylate) melatonin.

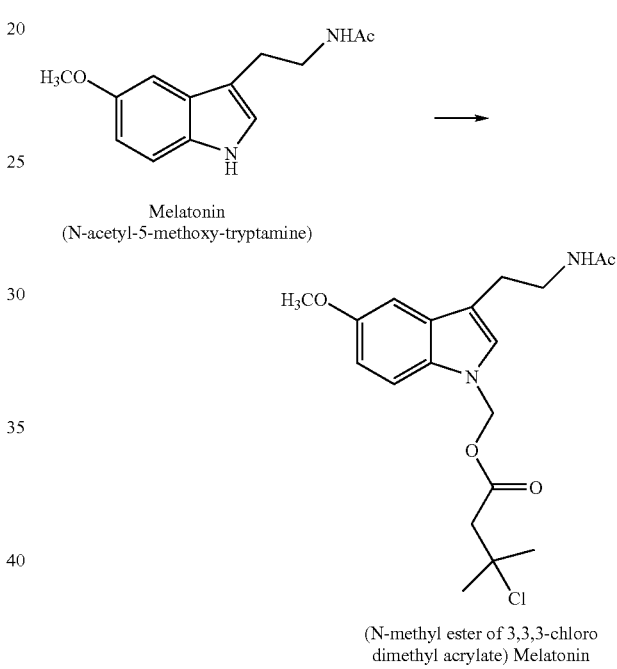

Synthesis of N-Acetyl Serotonin

N-acetyl serotonin was synthesized as follows. 100 mg (0.47 mmol) serotonin hydrochloride and 10 mL of pyridine were mixed in a 100 mL round-bottomed flask, and the solution was cooled to 0° C. under argon. Acetic anhydride (2.84 g, 28.4 mmol) was added slowly over 1 hr. After stirring at 0° C. for 20 hr the reaction was terminated by removing the volatile reagents under high vacuum. The remaining syrup was dissolved into 25 mL of methylene chloride and washed with 0.1 M HCl until the pH of the aqueous phase was less than 3. The organic phase was dried under anhydrous sodium sulfate, filtered and concentrated to yield a syrup. To this syrup was added 25 mL of aqueous isopropyl alcohol (50 wt%) and the solution was cooled to 0° C. Sodium hydroxide (1 mL of a 1.0 mM solution) was added and stirred at 0° C. for 4 hr. The solution was neutralized with acetic acid, concentrated and filtered through a short plug of silica gel with ether, concentrated and recrystallized from benzene/chloroform to yield 27 mg (0.11 mmol) of N-acetyl serotonin.

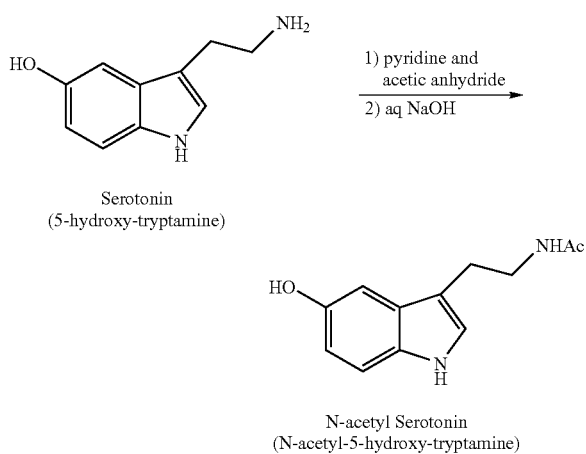

Serotonin
(5-hydroxy-tryptamine)

N-acetyl Serotonin
(N-acetyl-5-hydroxy-tryptamine)

It should be understood that the foregoing disclosure emphasizes certain specific embodiments of the invention and that all modifications or alternatives equivalent thereto are within the spirit and scope of the invention as set forth in the appended claims.

What is claimed is:

1. A pharmaceutical composition comprising:
   a) a psychotropic, neurotropic or neurological drug, or an antibiotic, antibacterial, antimycotic, antiviral, antiproliferative or antineoplastic drug, wherein the drug is L-dopa, hydroxytryptamine, amantadine, benztropine, bromocryptine, diphenhydramine, levadopa, pergolid, trihexphenidyl, ethosuximide, valproic acid, carbamazepine, 10-hydroxycarbamazepine, 11-hydroxycarbamazepine, primidone, gabapentin, lamotrigine, felbamate, paramethadione, trimethadione, phenothiazine, thioxantheme, clozapine, haldoperidol, loxapine, a benzodiazapene antidepressant of the norepinephrine reuptake inhibitor type, a monoamine oxidase inhibitor, carotene, glutathione, N-acetylcysteine, methotrexate, azidothymidine, dideoxyinosine, dideoxycytosine, acyclovir, or gancyclovir;
   b) 5-hydroxytryptophan, serotonin, or melatonin; and
   c) a spacer having a first linker functional group and a second linker functional group,
   wherein the spacer has a first end and a second end and wherein 5-hydroxytryptophan, serotonin, or melatonin is attached to the first end of the spacer through the first linker functional group and the drug is attached to the second end of the spacer through the second linker functional group.

2. A pharmaceutical composition according to claim 1 wherein the spacer allows the drug to act without being released at an intracellular site and wherein the first linker functional group is strong and the second linker functional group is weak.

3. A pharmaceutical composition according to claim 1 wherein the spacer allows the facilitated hydrolytic release of the drug at an intracellular site and wherein the first linker functional group is strong and the second linker functional group is weak.

4. A pharmaceutical composition according to claim 1 wherein the spacer allows the facilitated enzymatic release of the drug at an intracellular site and wherein the first linker functional group is strong and the second linker functional group is weak.

5. A pharmaceutical composition comprising:
   a) a psychotropic, neurotropic or neurological drug, or an antibiotic, antibacterial, antimycotic, antiviral, antiproliferative or antineoplastic drug, wherein the drug is L-dopa, hydroxytryptamine, amantadine, benztropine, bromocryptine, diphenhydramine, levadopa, pergolid, trihexphenidyl, ethosuximide, valproic acid, carbamazepine, 10-hydroxycarbamazepine, 11-hydroxycarbamazepine, primidone, gabapentin, lamotrigine, felbamate, paramethadione, trimethadione, phenothiazine, thioxantheme, clozapine, haldoperidol, loxapine, a benzodiazapene antidepressant of the norepinephrine reuptake inhibitor type, a monoamine oxidase inhibitor, carotene, glutathione, N-acetylcysteine, methotrexate, azidothymidine, dideoxyinosine, dideoxycytosine, acyclovir, or gancyclovir,
   wherein the drug has a first functional linker group, and
   b) 5-hydroxytryptophan, serotonin, or melatonin,
   having a second functional linker group,
   wherein the drug is covalently linked to 5-hydroxytryptophan, serotonin, or melatonin by a chemical bond between the first and second functional linker groups.

6. A pharmaceutical composition according to claim 5 wherein the first functional linker group is a hydroxyl group, a primary or secondary amino group, a phosphate group or a carboxylic acid group.

7. A pharmaceutical composition according to claim 5 wherein the second functional linker group is a hydroxyl group, a primary or secondary amino group, a phosphate group or a carboxylic acid group.

* * * * *